[19] United States Patent

Carnmalm et al.

[11] 4,053,637

[45] Oct. 11, 1977

[54] COMPOUNDS OF DIPHENYLCYCLOPENTYLAMINE TYPE AND METHODS FOR THEIR USES

[75] Inventors: Bernt Sigfrid Emanuel Carnmalm; Ulf Henrik Anders Lindberg, both of Sodertalje; Tomas de Paulis, Gnesta; Svante Bertil Ross, Sodertalje; Nils-Erik Stjernstrom, Sodertalje; Carl Bengt Johan Ulff, Sodertalje; Sven-Ove Ogren, Sodertalje, all of Sweden

[73] Assignee: Astra Lakemedal Aktiebolag, Sodertalje, Sweden

[21] Appl. No.: 579,049

[22] Filed: May 20, 1975

Related U.S. Application Data

[63] Continuation of Ser. No. 257,707, May 30, 1973, abandoned.

[30] Foreign Application Priority Data

June 11, 1971  Sweden .................................. 7631/71

[51] Int. Cl.² .......................... A01N 9/20; A01N 9/24
[52] U.S. Cl. .................................. 424/330; 260/501.1; 260/501.12; 260/501.18; 260/501.19; 260/501.21; 260/515 R; 260/544 N; 260/558 R; 260/570 R; 260/571; 260/576; 260/578; 260/590 C; 424/316
[58] Field of Search .................... 260/570 R; 424/316, 424/330

[56] References Cited

U.S. PATENT DOCUMENTS 3,285,960  11/1966  Halverstadt .......................... 260/570
3,328,249  6/1967  Aceto et al. ...................... 260/570 X
3,376,312  4/1968  Unger et al. ..................... 260/570 X

OTHER PUBLICATIONS

Graham et al., "Journal of the Chemical Society" of London, p. 390 (1969).

Primary Examiner—Robert V. Hines
Attorney, Agent, or Firm—Brumbaugh, Graves, Donohue & Raymond

[57] ABSTRACT

Compounds of the formula

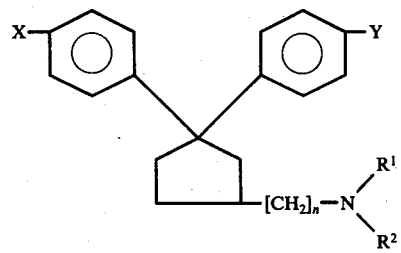

and pharmaceutically acceptable salts thereof, wherein X and Y are the same or different and each representing a hydrogen atom, a chloro or a methoxy group, $n$ is an integer 0 or 1 and $R^1$ and $R^2$ are the same or different and each representing a hydrogen atom or a methyl group; processes for their preparation; pharmaceutical preparations containing at least one of these compounds and the use thereof in the treatment of depressive states.

18 Claims, No Drawings

COMPOUNDS OF DIPHENYLCYCLOPENTYLAMINE TYPE AND METHODS FOR THEIR USES

This is a continuation, of application Ser. No. 257,707 filed May 30, 1973 and now abandoned.

This invention relates to new compounds of the diphenylcyclopentylamine type and methods for their preparation. The invention also relates to the preparation of pharmaceutical preparations containing such compounds and to methods for the pharmacological use of the compounds.

The main object of the invention is to provide compounds having psychopharmacological, especially antidepressive properties.

Depressions are considered to depend on changes in the biochemical processes of the brain which control the mood. The nature of this biochemical deficiency is largely unknown but in depressive states there is evidence for a decreased activity of monoaminergic brain neurons. The monoamines, noradrenaline (NA), dopamine (DA) and 5-hydroxytryptamine (5-HT), are of great interest in this respect.

It has been demonstrated that NA, DA and 5-HT are localised in three different types of neurones and may function as transmittors in the central nervous system. The monoamines are stored in special structures, granules, situated in enlargements of the nerve endings, varicosities. The varicosity is separated from the effector neuron by a space, the synaptic cleft or spatium. As a result of a nerve stimulation the transmittor is released from the granule into the synaptic cleft and reaches the receptor of the effector neuron and generates a nerve impulse. After impulse generation the amines are inactivated by mainly two mechanisms: a re-uptake mechanism at the cell membrane and enzymatic conversion by catechol-O-methyltransferase to form methylated metabolites. There is also an inactivating enzyme within the varicosities, monoamine oxidase (MAO), that is stored in the mitochondria and inactivates the amines intracellularly.

When MAO-inhibitors are administered, an increased amount of transmittor substance becomes available for release at the nerve ending.

Another way of increasing the amine levels at the receptor is exerted by the tricyclic antidepressants. It has been shown that this type of compounds inhibits the re-uptake mechanism of NA and 5-HT, and the antidepressive action is assumed to be related to the uptake inhibition of NA and 5-HT.

The over all clinical effect of the tricyclic antidepressants consists according to Kielholz (Deutsch Med.Wschr. 93, 1968) of three main components in various proportions:
1. Psychomotor activating or increase in drive
2. Elevation of mood
3. Relief of anxiety.

It has been proposed that the correlation between the clinical effects and the biochemical changes in the adrenergic neurones might be that the NA neurones are involved in psychomotor activity and the 5-HT-neurones are involved in the elevation of mood. The third component, relief of anxiety, may be caused by blockade of the NA and DA receptors, but probably not the 5-HT receptors. However, it should be pointed out that these theories are much simplified.

A compound frequently used for controlling depressions is imipramine (Tofranil ®)

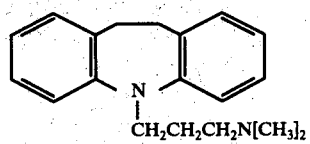

This compound is both mood elevating and psychomotor activating, but it possesses several disadvantages. It is anticholinergic and causes anticholinergic symptoms such as dryness of the mouth, tremor, tachycardia and sweating. In higher doses it can provoke serious heart arrythmias and in normal doses it can cause toxic interactions in persons with heart failures. Furthermore, another drawback of treatment with imipramine is the late onset of the antidepressive effect which effect is observable first after 3 weeks of treatment.

According to the present invention it has now been found that the above-mentioned disadvantages can be overcome by using compounds selected from the group consisting of compounds of the general formula

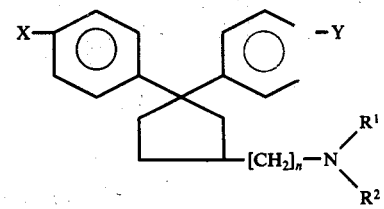

I wherein X and Y are the same or different and each representing a hydrogen atom, a chloro or a methoxy group, $n$ is an integer 0 or 1, and $R^1$ and $R^2$ are the same or different and each representing a hydrogen atom or a methyl group, and pharmaceutically acceptable acid addition salts thereof.

Compounds described above which contain an asymmetric carbon atom exist in the form of optically active forms, and can be resolved into their optical antipodes by well known methods such as by using optically active acids such as tartaric acid, camphor-10-sulphonic acid, dibenzoyl tartaric acid and the like.

Some of the compounds described above can exist as stereoisomers, which forms constitute a further aspect of this invention. Mixtures of such isomers can be separated by methods known to the state of the art.

The compounds described above can be used as mixtures of the above mentioned isomeric forms or in the form of pure isomers.

The compound of the invention, which is specially preferred is 1-amino-3,3-diphenylcyclopentane.

The compounds of this invention with the general formula I can be prepared according to different methods.

A. The compounds of the invention with the general formula

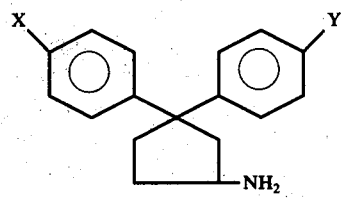

wherein X and Y have the meaning given above, can be obtained

B. The compounds of the invention with the general formula according to the reaction scheme

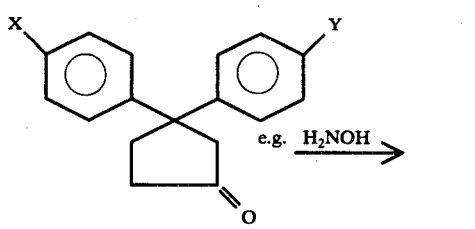

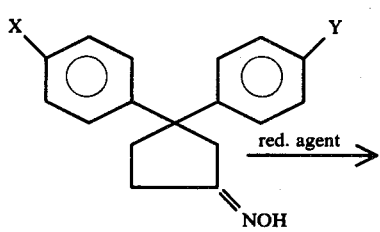

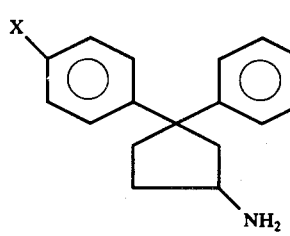

wherein X and Y have the meaning given above.

B. The compounds of the invention with the general formula

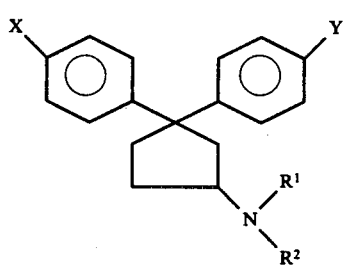

wherein X, Y, R¹ and R² have the meaning given above can be prepared according to the reaction scheme

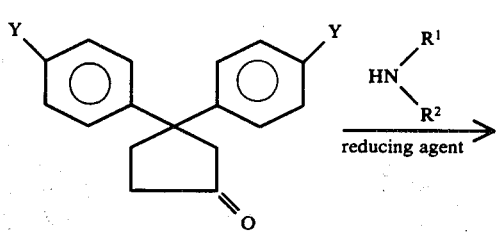

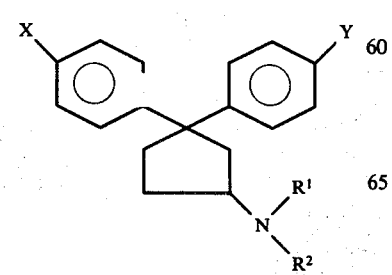

wherein X, Y, R¹ and R² have the meaning given above.

C. The compounds of the invention with the general formula

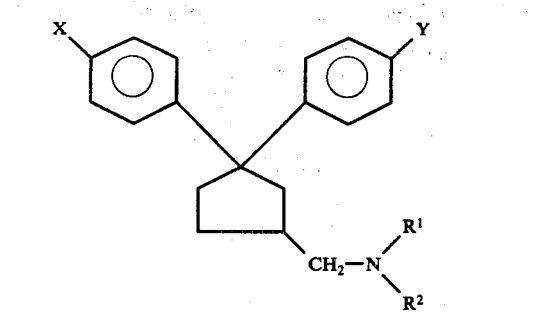

wherein X, Y, R¹ and R² have the meaning given above can be obtained according to the reaction scheme

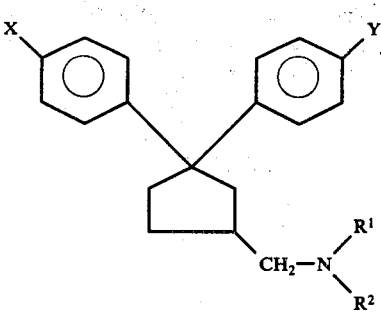

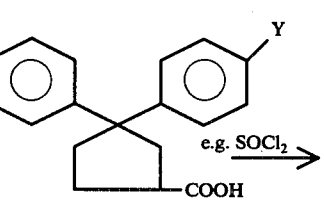

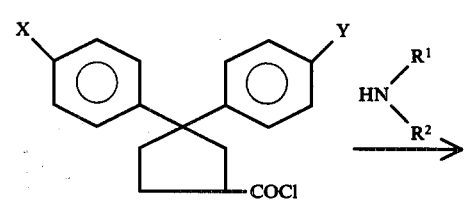

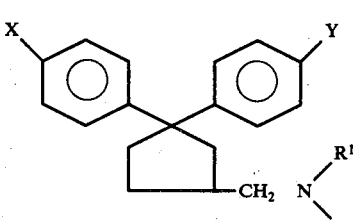

wherein X, Y, R¹ and R² have the meaning given above.

D. The compounds of the invention with the general formula

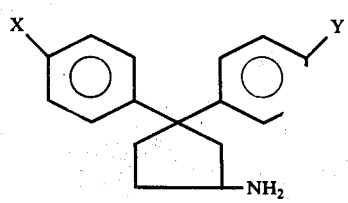

wherein X and Y have the meaning given above, can be obtained according to the reaction scheme

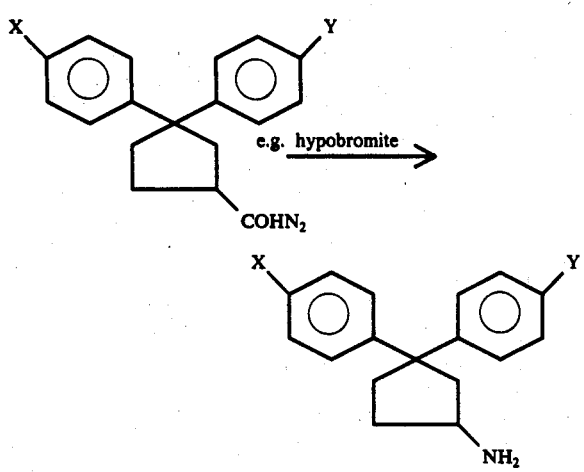

wherein X and Y have the meaning given above.

E. The compounds of the invention with the general formula

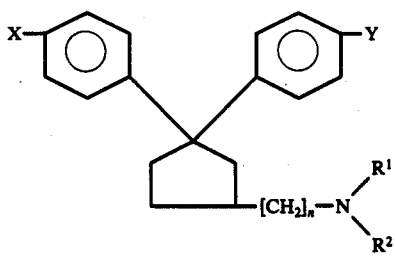

can be obtained by reacting a compound of the general formula

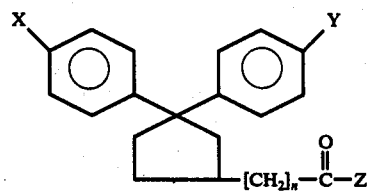

in which formulas X, Y, n, $R^1$ and $R^2$ have the previously given definition and Z is a hydroxy group, a halogen group, e.g. chlorine or another acid residue, e.g. an acid anhydride, with hydrozoic acid ($HN_3$) or an inorganic salt thereof according to the conditions of the Schmidt reaction, which gives a primary amine, and if a secondary or tertiary amine is desired converting the obtained primary amine in ways known per se to the corresponding secondary or tertiary amine.

In the cases where an intermediate acylic derivative or the like is obtained in any of the methods A - E hydrolysis is necessary to obtain the compounds of the formula I.

Both organic and inorganic acids can be employed to form non-toxic pharmaceutically acceptable acid addition salts of the compounds of this invention. Illustrative acids being sulfuric, nitric, phosphoric, hydrochloric, citric, acetic, lactic, tartaric, pamoic, ethanedisulfonic, sulfamic, succinic, cyclohexylsulfamic, fumaric, maleic and benzoic. These salts are readily prepared by methods known to the art.

In clinical practice the compounds of the present invention will normally be administered orally, or by injection, in the form of pharmaceutical preparations comprising the active ingredient either as a free base or as a pharmaceutically acceptable non-toxic, acid addition salt, e.g. the hydrochloride, lactate, acetate, sulfamate, and the like, in association with a pharmaceutically acceptable carrier. Accordingly, terms relating to the novel compounds of this invention, whether generically or specifically, are intended to include both the free amine base and the acid addition salts of the free base, unless the context in which such terms are used, e.g. in the specific examples, would be inconsistent with the broad concept. The carrier may be a solid, semisolid or liquid diluent or capsule. These pharmaceutical preparations constitute a further aspect of this invention. Usually the active substance will constitute between 0.1 and 95% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid fine grain carrier, e.g., lactose, saccharose, sorbitol, mannitol, starches such as potato starch, corn starch or amylopectin, cellulose derivatives, or gelatin and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g., gum arabic, gelatin, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatin capsules (pearl-shaped closed capsules) consisting of gelatin and, for example, glycerol or similar closed capsules, the active substance may be admixed with a vegetable oil. Hard gelatin capsules may contain granulates of the active substance in combination with solid, fine grain carriers such as lactose, saccharose, sorbitol, mannitol, starches (e.g. potato starch, corn starch or amylopectin), cellulose derivatives or gelatin.

Liquid preparations for oral application may be in the form of syrups or suspensions, for example, solutions containing from about 0.2% to about 20% by weight of the active substance herein described, the balance being sugar and a mixture of ethanol, water, glycerol and propyleneglycol. Optionally such liquid preparations may contain colouring agents, flavouring agents, saccharine and carboxymethylcellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules.

In therapeutical treatment the suitable diurnal doses of the compounds of the invention are 5–500 mg for oral application, preferentially 50–250 mg and 1–100 mg for parenteral application, preferentially 10–50 mg.

The following examples will further illustrate the invention.

EXAMPLE 1

1-Amino-3,3-diphenylcyclopentane [PUB 105]

a. 3,3-diphenylcyclopentanone (0.100 mole), hydroxylamine hydrochloride (0.250 mole), ethanol (100 ml) and pyridine (100 ml) were refluxed for 2 hours. The solvents were removed, water and chloroform added and the organic layer was separated. Chloroform was removed and the residue recrystallized from 90% ethanol. Yield 3,3-diphenylcyclopentanone oxime (85%). M.p. 113°–115° C.

b. The oxime (0.100 mole) was dissolved in ether (500 ml) and cooled to 5° C. Lithium aluminium hydride (0.250 mole) was added portionwise and the mixture was refluxed for 2 hours. After cooling, saturated sodium sulfate solution (75 ml) was added dropwise and the white precipitate was filtered off. The ether solution was extracted with 1 N HCl, the acid solution made alkaline and extracted with ether. After removing the ether the residual 1-amino-3,3-diphenylcyclopentane crystallized. M.p. 58°–60° C. Yield: 90%. Hydrochloride: M.p. 181°–182° C.

According to the method described in Example 1 the following compounds were prepared:

1-amino-3-(4-chlorophenyl)-3-phenylcyclopentane [PUN 122] Hydrochloride m.p. 251°–254° C
1-amino-3,3-di(4-chlorophenyl)cyclopentane [PUT 108] Hydrochloride m.p. 207°–209° C
1amino-3-(4methoxyphenyl)-3-phenylcyclopentane [PUT 104] Hydrochloride m.p. 230°–232° C.

EXAMPLE 2

1-dimethylamino-3,3-diphenylcyclopentane [PUB 112 ]

To dimethylamine (1.00 mole) at −20° C was slowly added formic acid (0.25 mole). 3,3-diphenylcyclopentanone (0.100 mole) dissolved in N,N-dimethylformamide (100 ml) was added and the temperature allowed to rise. After boiling ,at 140° C for 5 hours the solution was cooled. Benzene and water was added and the organic phase was extracted with 1 N HCl. The acid solution was made alkaline and extracted with benzene and ether. Removal of the solvents and distillation yielded the amine (80%). B.p. 150° 005 C/O. mm. M.p. 62°–64° C. Hydrochloride: M.p. 159°–160° C.

According to the method described in Example 2 the following compounds were prepared:

1-methylamino-3,3-diphenylcyclopentane [PUB 107] Hydrochloride m.p. 197°–199° C
1-methylamino-3-(4-chlorophenyl)-3-phenylcyclopentane [PUN 125] Hydrochloride m.p. 209°–211° C
1-dimethylamino-3-(4-chlorophenyl)-3-phenylcyclopentane [PUN 123] Hydrochloride m.p. 168°–170° C.

EXAMPLE 3

1-aminomethyl-3,3-diphenylcyclopentane [PUE 119]
3,3-diphenylcyclopentanecarboxylic acid (0.100 mole) and thionyl chloride (100 ml) were refluxed for 2 hours. Thionyl chloride was removed and the residue was dissolved in ether. Ammonia was led in for 2 hours, ammonium chloride filtered off and washed with benzene. The solvents were removed and the residual 3,3-dphenylcyclopentanecarboxylic acid amide crystallized from benzene/ether M.p. 118°–119° C. Yield: 55%.

The above amide (0.100 mole), dissolved in tetrahydrofuran (200 ml) was added dropwise to lithium aluminium hydride (0.250 mole) in tetrahydrofuran (200 ml). The mixture was refluxed for 3 hours, cooled, water and 15% NaOH was added and the mixture filtered. The filtrate was dried, the solvent removed and the residue distilled. B.p. 143° – 145° C C/0.2 mm Hg. $n_D^{25}$ = 1.5910. Yield 75%. Hydrochloride: m.p. 186° – 187° C.

According to the method described in Example 3 the following compounds were prepared:

1methylaminomethyl-3,3-diphenylcyclopentane [PUE 122] Hydrochloride m.p. 221° – 223° C.
1dimethylaminomethyl-3,3-diphenylcyclopentane [PUE 117] Hydrochloride m.p. 220° – 222° C.

EXAMPLE 4

1-Amino-3,3-diphenylcyclopentane

Method D

To sodium (0.200 mole) dissolved in methanol (50 ml) was added 3,3-diphenylcyclopentanecarboxylic acidamide (0.100 mole) in methanol (30 ml ). Bromine (0.100 mole) was added dropwise at 0° C. The mixture was refluxed for 15 min and the methanol removed. Water (100 ml) was added, the solution made alkaline with ammonia and extracted with ether and benzene. The solvents were removed and the residue was refluxed in ethanol (500 ml) and 10 N NaOH (100 ml) for 4 hours. Ethanol was removed and the aqueous phase extracted with ether.

The crude base was obtained after evaporation of the solvent. Yield: 50%.

EXAMPLE 5

1-Amino-3,3-diphenylcyclopentane

Method E

To 3,3-Diphenylcyclopentanecarboxylic acid (0.100 mole), in water (20 ml) and acetone (75 ml) at 10° C was added triethylamine (0.110 mole) in acetone (75 ml). Ethyl chloroformate (0.120 mole) in acetone (50 ml) was added at 5° C. After 1 hour sodium azide (1.50 mole) in water (30 ml) was added at 0° C.

After stirring at 0° C for 1 hour the mixture was poured into water (500 ml) and the aqueous phase was extracted with ether. The ether was removed and the residue was heated with 70% aqueous acetic acid at 100° C for 2 hours. Concentrated hydrochloric acid was added and the mixture was heated at 100° C for 15 hours. The solution was cooled and poured into ice-water (500 ml) and made alkaline. The aqueous phase was extracted with ether and, after evaporation of the solvent, the residue was distilled. Yield: 65% B.p.

145°/0.1 mm Hg. M.p. 72° - 73° C. Hydrochloride: m.p. 181° - 183° C.

EXAMPLE 6

Preparation of tablets a. Each tablet contains:

1-amino-3,3-diphenylcyclopentane-HCl: 10 mg
Lactose: 60 mg
Starch: 29 mg
Magnesium stearate: 1 mg.

The powders are mixed and directly compressed to tablets with a diameter of 6 mm.

The active substance shown above may be replaced by other pharmaceutically acceptable acid addition salts according to the invention.

b. 1-aminomethyl-3,3-diphenylcyclopentane: 50 mg
Aerosil ® (silicium dioxide): 20 mg
Lactose: 100 mg
Starch: 30 mg
Magnesium stearate: 2 mg.

The active principle is mixed with the Aerosil ®. This mixture is added to the other powders. Tablets are compressed with a diameter of 10 mm.

The active substance shown above may be replaced by other pharmaceutically acceptable acid addition salts according to the invention.

EXAMPLE 7

Preparation of capsules a. 1-amino-3,3-diphenylcyclopentane: 20 mg
Peanut oil: 60 mg.

The solution is filled into soft gelatine capsules. Each capsule containing 20 mg of the active principle.

The active substance shown above may be replaced by other pharmaceutically acceptable acid addition salts according to the invention.

b. 1-amino-3,3-diphenylcyclopentane: 10 mg Polyoxyethylene sorbitan monooleate 100 mg.

The capsules are made as described above.

The active substance shown above may be replaced by other pharmaceutically acceptable acid addition salts according to the invention.

PHARMACOLOGICAL METHODS

A. Biochemical tests

1. Inhibition of the uptake of tritiated 5-HT in vitro and in vivo

The method is described by Ross and Renyi in European Journal of Pharmacology 7 (1969), 270-277. Tricyclic antidepressant drugs of type imipramine given in vivo to mice decrease the uptake of $^3$H-5-HT in vitro. The drugs were administered intraperitoneally half an hour before the animals were killed and the midbrain was taken out and sliced and incubated in a mixture consisting of, per 100 mg of brain slices, 0.2 μmole of $^3$H-5-HT and 1 μmole of glucose in 2 ml of Krebs-Henseleit buffer, pH 7.4. The incubation time was 5 minutes with 5 minutes of preincubation before $^3$H-5-HT was added. The radioactive $^3$H-5-HT taken up in the slices was extracted with ethanol and the amount was determined by liquid scintillation. The dose producing 50 percent decrease of the active uptake ($ED_{50}$) was determined graphically from dose response curves. Active uptake is defined as that part of the radioactive uptake which is inhibited by a high concentration of cocaine. All doses were given at least to four animals.

2. Inhibition of the uptake of tritiated noradrenaline in vitro and in vivo

The method is found in European Journal of Pharmacology 2 (1967), 181-186. The animals were killed half or one hour after the administration of the drugs in vivo (i.p). The slices, made from cortex, were preincubated for 5 minutes and incubated with 0.1 μmole per ml of $^3$H-noradrenaline for further 5 minutes. The incubation mixture consisted of 0.2 μmole of $^3$H-NA and the brain slices in 2 ml of Krebs-Henseleits buffer, pH 7.4. The radioactive $^3$H-NA taken up in the slices was extracted with ethanol and the amount was determined by liquid scintillation. The dose producing 50 percent decrease of the active uptake ($ED_{50}$) was determined graphically from dose response curves. At least four animals were used at each dose level.

B. Pharmacological tests 1. 5-HTP response potentiation test

Inhibition of the uptake of 5-HT potentiates the effects of administered 5-hydroxytryptophane (5-HTP) probably by increasing the amount of 5-HT at the receptor. Three mice are given the test drugs 1 hour (or 4, 24 hours) before dl-5-HTP 90 mg/kg i.v. 5-HTP alone gives only a weak behavioural syndrome but in pretreated mice there is seen a characteristic behavioural syndrome, which comes within 5 minutes: tremor, lordosis, abduction of the hindlegs, head-twitches.

These small movements are quantitatively measured in an activity box, type Animex, which can distinquish between small and gross movements. The activity is measured during 20 minutes and only in the case the animals have a fullblown syndrome. Each group consists of 3 animals and at least 4 groups were tested at 25 mg/kg i.p. Control groups receiving imipramine (Tofranil ®) are used as reference, since imipramine constantly potentiated dl-5-HTP.

2. Dopa response potentiation test

Inhibition of monoamine oxidase together with blockage of the uptake of NA potentiate the effects of administrated l-Dopa. This test is developed by G. M. Everett (Antidepressant Drugs, ed. S. Carattini, 1966).

Mice in groups of 3 are pretreated with Pargyline ® 40 mg/kg p.o. about 10-16 hours before the test. The test drugs are given i.p. one or four hours before l-Dopa 100 mg/kg i.p. The mice are observed for 1 hour after l-Dopa administration. l-Dopa gives a characteristic syndrome which is scored as follows:

1. piloerection, slight salivation, slight increased motor activity
2. piloerection, salivation, marked increased motor activity and irritability
3. piloerection, profuse salivation, marked irritability and reactivity, jumping, squeaking, fighting.

The control groups are Amitriptyline (20 mg/kg i.p. 4 hours before l-Dopa) and saline (1 hour before l-Dopa). Amitriptyline always scores three at this dose whereas saline gives a one score. The test drugs were all tested at 10 mg/kg i.p.

MOTOR ACTIVITY IN MICE

The exploratory activity of mice was recorded in a locomotion cage in which the movements were counted each time the animals cross-circuits an electrical current in the bottom plate. The activity was recorded for 10 minutes 1 hour after the administration of the drug. The animals were tested individually. Groups of six mice were used and the mice were only used once. The activity was expressed in percent of the activity of control groups ran simultaneously.

ACUTE TOXICITY, BEHAVIOUR AND ANTICHOLINERGIC EFFECT (MYDRIASIS) IN MICE

The compounds were given by intravenous route to 3 mice. $LD_{50}$ is the dose which kills 50% of the animals within 24 hours. Siezures, gait, sedation and grip strength were recorded. Pupil width (mydriasis) which reveals peripheral anticholinergic action was measured in green light. These data are expressed in percent of control values 10 minutes after injection. $PD_{200}$ is the dose which increases the pupil by 200%.

DRUG INDUCED ARRHYTHMIA IN RATS: ECG CHANGES AND $LD_{50}$

Rats were infused intravenously with test drugs and relevant reference compounds. The doses were increased step-wise. The first dose causing ECG changes of any type was noted, and thereafter the doses were increased up to the lethal dose.

relates well with the uptake inhibition of 5-hydroxytryptamine and noradrenaline. The intravenous toxicity of the compounds is about comparable to that of imipramine. PUB 105 has much weaker peripheral anticholinergic effects than imipramine, causes ECG changes in a dose 3 times higher than that of imipramine and is considerably less toxic in rats. These results indicate that in this series of compounds it is possible to differentiate the uptake inhibition from the unwanted side effects and to find potent and selective inhibitors of the amine uptake in the brain.

What we claim is:

1. A pharmaceutical preparation for selectively blocking noradrenaline uptake by adrenergic nerve terminals, said preparation containing as an active ingredient an effective amount of a compound having the structural formula

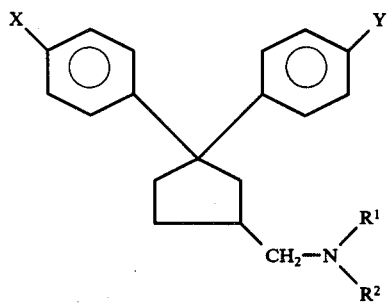

or a pharmaceutically acceptable acid addition salt thereof, wherein X and Y are the same or different and each represents a member selected from the group con-

| Substance | Inhibition (50 %) of uptake | | | | 5-HTP[3] potentiation 25mg/kg i.p. | | L-DOPA[4] potentiation 10 mg/kg i.p. | | Motor activity $ID_{50}$ mg/kg i.p. | Mydriasis $PD_{200}$ mg/kg i.v. | Acute toxicity $LD_{50}$ mg/kg i.v. | $Ld_{50}$ i.v. rat | ECG changes i.v. rat |
|---|---|---|---|---|---|---|---|---|---|---|---|---|---|
| | in vitro | | in vivo | | | | | | | | | | |
| | 5-HT[1] | NA[2] | 5-HT[1] | NA[2] | 1h | 4h | 1h | 4h | | | | | |
| | μg/ml | | mg/kg i.p. | | | | | | | | | | |
| PUB 105 | 0.18 | 0.15 | 10–20[5] | 20[5] | 12.5 | 25 | 3 | 3 | >50 | 19 | 22 | 58 | 14 |
| PUB 107 | — | — | >40 | — | 0 | | 2 | 2 | >50 | 15 | 30 | | |
| PUB 112 | — | — | >40 | — | 25 | | 2.5 | 2 | >50 | <1 | 18 | | |
| PUE 119 | 0.34 | 0.025 | >40 | 6.5 | 0 | | 1.5 | 1.5 | >50 | 2.5 | 22 | | |
| PUE 122 | 4.2 | 0.05 | >40 | 5.5 | 0 | | 3 | 3 | >50 | >12.5 | 15 | | |
| PUE 117 | 3.6 | 2.3 | >40 | 17 | 0 | | 3 | 1.5 | >50 | <1 | 30 | | |
| PUN 122 | 0.3 | — | 20 | — | 25 | | 3 | 3 | >50 | >12.5 | 15 | | |
| PUE 119 | 1 | 1 | 40 | 30 | 25 | 0 | 3 | 3 | >50 | <10 | 30 | | |
| PUN 125 | — | — | — | — | 0 | | 1 | 1 | | | | | |
| PUT 108 | 1 | 2.5 | >40 | >40 | >25 | >10 | | | >50 | >23 | 23 | | |
| PUT 104 | 0.5 | 1 | >40 | >40 | >25 | >10 | | | | >40 | >40 | | |
| Imipramine | 0.10 | 0.06 | 24 | 6 | 25 | 0 | 2 | 1 | 45 | 13 | 28 | 9.3 | 4.7 |

[1]5-HT = 5-hydroxytryptamine 10⁻⁷M
[2]NA = dl-noradrenaline 10⁻⁷M
[3]5-HTP = 1-5-hydroxytryptophane
[4]1-DOPA = 1-3,4-dihydroxyphenyl-alanine
[5]long duration
0 = without effect

EVALUATION OF THE RESULTS OBTAINED IN THE PHARMACOLOGICAL TESTS

The results are summarized in the table.

The compounds of the invention block with both the uptake of noradrenaline and 5-hydroxytryptamine in brain slices in vitro and in vivo. Two compounds PUE 119 and PUE 122 are about as effective as imipramine in blocking the uptake of noradrenaline in vivo. PUB 105 is about twice as potent as imipramine on the inhibition of 5-HT uptake whereas PUN 122 is slightly more effective, and both drugs inhibit the membrane pump for a much longer time. As for PUB 105 and PUN 122 the uptake inhibition increases with time and is maximal after 4 hours and is still pronounced after 16 hours. The interaction with 5-hydroxytryptophane and 1-dopa corsisting of a hydrogen atom, a chloro group and a methoxy group; and $R^1$ and $R^2$ are the same or different and each represents a member selected from the group consisting of a hydrogen atom and a methyl group, together with a pharmaceutically acceptable carrier.

2. A pharmaceutical preparation according to claim 1, wherein the compound is

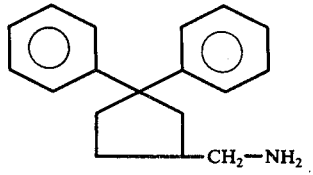

or a pharmaceutically acceptable acid addition salt thereof.

3. A pharmaceutical preparation according to claim 1, wherein the compound is

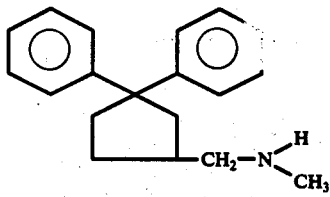

or a pharmaceutically acceptable acid addition salt thereof.

4. A pharmaceutical preparation according to claim 1, wherein the compound is

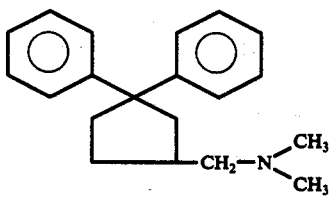

or a pharmaceutically acceptable acid addition salt thereof.

5. A method for selectively blocking noradrenaline uptake by adrenergic nerve terminals which comprises administering to a host having symptoms of depression an amount effective to provide said selective blocking of a compound having the formula

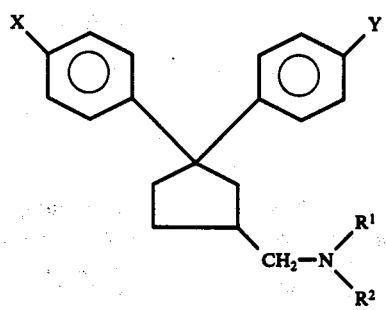

or a pharmaceutically acceptable acid addition salt thereof, wherein X and Y are the same or different and each represents a member selected from the group consisting of a hydrogen atom, a chloro group and a methoxy group; and $R^1$ and $R^2$ are the same or different and each represents a member selected from the group consisting of a hydrogen atom and a methyl group.

6. A method according to claim 5, wherein the compound is

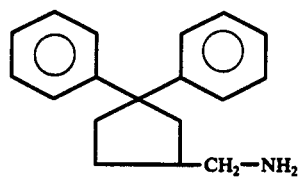

or a pharmaceutically acceptable acid addition salt thereof.

7. A method according to claim 5, wherein the compound is

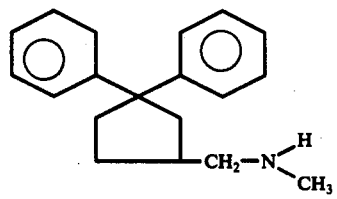

or a pharmaceutically acceptable acid addition salt thereof.

8. A method according to claim 5, wherein the compound is

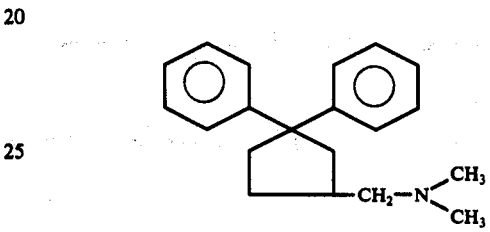

or a pharmaceutically acceptable acid addition salt thereof.

9. A compound of the formula

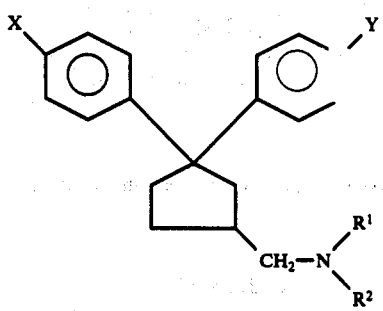

wherein X and Y are the same or different and each represents a member selected from the group consisting of a hydrogen atom, a chloro group or a methoxy group; and $R^1$ and $R^2$ are the same or different and each represents a member selected from the group consisting of a hydrogen atom and a methyl group, and pharmaceutically acceptable acid addition salts thereof.

10. A compound according to claim 9 in the form of a pure isomer.

11. A compound according to claim 9 in the form of an optically pure isomer.

12. A compound according to claim 9 having the formula

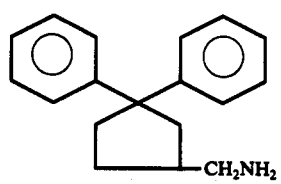

or a pharmaceutically acceptable acid addition salt thereof.

13. A compound according to claim 9 having the formula

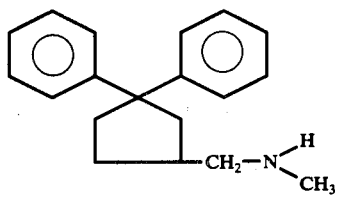

or a pharmaceutically acceptable acid addition salt thereof.

14. A compound according to claim 9 having the formula

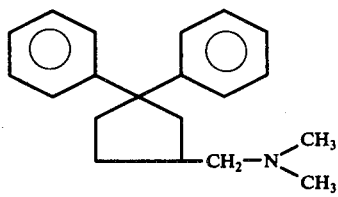

or a pharmaceutically acceptable acid addition salt thereof.

15. A pharmaceutical preparation for selectively blocking noradrenaline uptake by adrenergic nerve terminals, said preparation containing as an active ingredient an effective amount of a compound having the structural formula

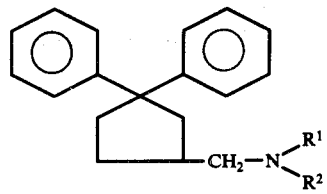

or a pharmaceutically acceptable acid addition salt thereof, wherein $R^1$ and $R^2$ are the same or different and each represents a member selected from the group consisting of a hydrogen atom and a methyl group, together with a pharmaceutically acceptable carrier.

16. A method for selectively blocking noradrenaline uptake by adrenergic nerve terminals which comprises administering to a host having symptoms of depression an amount effective to provide said selective blocking of a compound having the formula

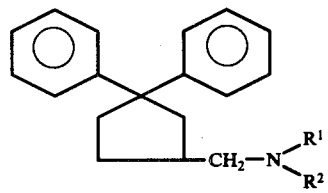

or a pharmaceutically acceptable acid addition salt thereof, wherein $R^1$ and $R^2$ are the same or different and each represents a member selected from the group consisting of a hydrogen atom and a methyl group.

17. A compound of the formula

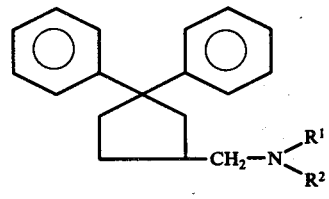

wherein $R^1$ and $R^2$ are the same or different and each represents a member selected from the group consisting of a hydrogen atom and a methyl group, and pharmaceutically acceptable acid addition salts thereof.

18. A compound according to claim 17 in the form of an optically pure isomer.

* * * * *

UNITED STATES PATENT AND TRADEMARK OFFICE
CERTIFICATE OF CORRECTION

PATENT NO. : 4,053,637
DATED : October 11, 1977
INVENTOR(S) : Bernt Sigfrid Emanuel Carnmalm et al.

It is certified that error appears in the above-identified patent and that said Letters Patent are hereby corrected as shown below:

Column 2, lines 26-29, the portion of the formula reading

" 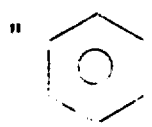 -Y "   should read   -- 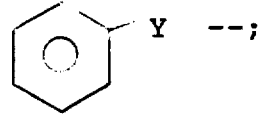 --;

Column 3, lines 50-54, the formula

" 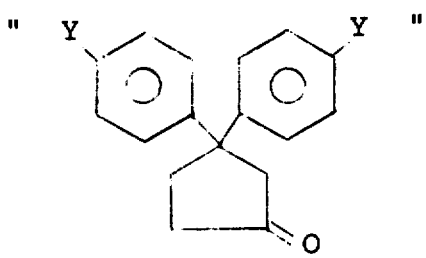 "   should read   -- 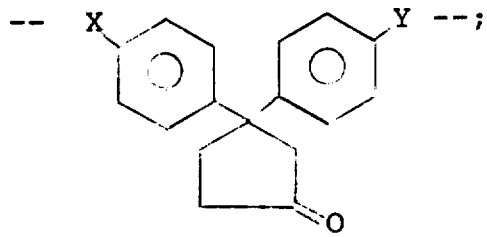 --;

Column 3, lines 58-62, the portion of the formula reading

" X 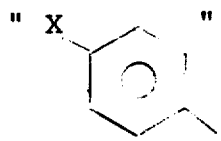 "   should read   -- X 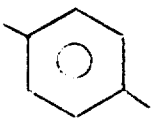 --;

Column 4, lines 58-62, the portion of the formula reading

" 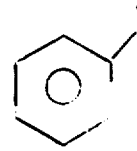 Y "   should read   --  Y --;

UNITED STATES PATENT AND TRADEMARK OFFICE
CERTIFICATE OF CORRECTION

PATENT NO. : 4,053,637              Page 2 of 3
DATED     : October 11, 1977
INVENTOR(S) : Bernt Sigfrid Emanuel Carnmalm et al.

It is certified that error appears in the above-identified patent and that said Letters Patent are hereby corrected as shown below:

Column 8, line 25, "1methylaminomethyl" should read -- 1-methylaminomethyl --;
line 27, "1dimethylaminomethyl" should read -- 1-dimethylaminomethyl --;

Column 12, line 59, in claim 2, "claim 1" should read -- claim 15 --;

Column 13, line 3, in claim 3, "claim 1" should read -- claim 15 --;
line 17, in claim 4, "claim 1" should read -- claim 15 --;
line 58, in claim 6, "claim 5" should read -- claim 16 --;

Column 13, lines 7-10, the portion of the formula reading "  " should read --  --;

Column 14, line 3, in claim 7, "claim 5" should read -- claim 16 --;
line 17, in claim 8, "claim 5" should read -- claim 16 --;
lines 34-38, in claim 9, the portion of the formula reading " - Y " should read -- - Y --;
line 58, in claim 12, "claim 9" should read -- claim 17 --;

UNITED STATES PATENT AND TRADEMARK OFFICE
CERTIFICATE OF CORRECTION

PATENT NO. : 4,053,637

DATED : October 11, 1977

INVENTOR(S) : Bernt Sigfrid Emanuel Carnmalm et al.

It is certified that error appears in the above-identified patent and that said Letters Patent are hereby corrected as shown below:

Column 15, line 5, in claim 13, "claim 9" should read -- claim 17 --; line 25, in claim 14, "claim 9" should read -- claim 17 --.

Signed and Sealed this

Thirtieth Day of May 1978

[SEAL]

Attest:

RUTH C. MASON
Attesting Officer

LUTRELLE F. PARKER
Acting Commissioner of Patents and Trademarks